US012076361B2

(12) United States Patent
McNeff et al.

(10) Patent No.: US 12,076,361 B2
(45) Date of Patent: Sep. 3, 2024

(54) COMPOSITIONS WITH AGENTS FOR MITIGATING METHANOGENESIS IN ANIMALS AND RELATED METHODS

(71) Applicant: SarTec Corporation, Anoka, MN (US)

(72) Inventors: Larry C. McNeff, Anoka, MN (US); Clayton V. McNeff, Andover, MN (US); Peter G. Greuel, Anoka, MN (US); Bingwen Yan, Shoreview, MN (US); Anthony Roy Jenks, Minneapolis, MN (US)

(73) Assignee: SarTec Corporation, Anoka, MN (US)

( * ) Notice: Subject to any disclaimer, the term of this patent is extended or adjusted under 35 U.S.C. 154(b) by 183 days.

(21) Appl. No.: 17/484,389

(22) Filed: Sep. 24, 2021

(65) Prior Publication Data
US 2022/0088110 A1 Mar. 24, 2022

Related U.S. Application Data

(60) Provisional application No. 63/082,906, filed on Sep. 24, 2020.

(51) Int. Cl.
A61K 36/898 (2006.01)
A61K 9/00 (2006.01)
A61K 31/10 (2006.01)
A61K 31/122 (2006.01)
A61K 31/192 (2006.01)
A61K 31/7048 (2006.01)
A61K 36/185 (2006.01)
A61K 36/21 (2006.01)
A61K 36/22 (2006.01)
A61K 36/48 (2006.01)
A61K 36/708 (2006.01)
A61K 36/752 (2006.01)
A61K 36/77 (2006.01)
A61K 36/81 (2006.01)
A61K 36/82 (2006.01)
A61K 36/886 (2006.01)
A61K 36/8945 (2006.01)
A61K 36/896 (2006.01)
A61K 36/8962 (2006.01)
A61K 36/8965 (2006.01)
A61P 1/14 (2006.01)

(52) U.S. Cl.
CPC .......... *A61K 36/898* (2013.01); *A61K 9/0056* (2013.01); *A61K 31/10* (2013.01); *A61K 31/122* (2013.01); *A61K 31/192* (2013.01); *A61K 31/7048* (2013.01); *A61K 36/185* (2013.01); *A61K 36/21* (2013.01); *A61K 36/22* (2013.01); *A61K 36/48* (2013.01); *A61K 36/708* (2013.01); *A61K 36/752* (2013.01); *A61K 36/77* (2013.01); *A61K 36/81* (2013.01); *A61K 36/82* (2013.01); *A61K 36/886* (2013.01); *A61K 36/8945* (2013.01); *A61K 36/896* (2013.01); *A61K 36/8962* (2013.01); *A61K 36/8965* (2013.01); *A61P 1/14* (2018.01)

(58) Field of Classification Search
CPC .... A61K 36/898; A61K 9/0056; A61K 31/10; A61K 31/122; A61K 31/192; A61K 31/7048; A61K 36/185; A61K 36/21; A61K 36/22; A61K 36/48; A61K 36/708; A61K 36/752; A61K 36/77; A61K 36/81; A61K 36/82; A61K 36/886; A61K 36/8945; A61K 36/896; A61K 36/8962; A61K 36/8965; A61K 9/0068; A61P 1/14; Y02P 60/22; Y02P 60/87; A23K 10/30; A23K 10/37; A23K 20/105; A23K 20/111; A23K 20/132; A23K 20/137; A23K 20/163; A23K 50/10
See application file for complete search history.

(56) References Cited

U.S. PATENT DOCUMENTS 4,388,327 A 6/1983 Cummins
5,139,779 A 8/1992 McNeff
(Continued)

FOREIGN PATENT DOCUMENTS

DE 102006042149 A1 * 5/2007 ............ A23K 10/30
EP 1088483 4/2001
WO 03056935 7/2003

OTHER PUBLICATIONS

"Sevarin® with Sarsaponin: gets 'em from feedlot to market faster, more profitably", Product Brochure, DPI Distributors Processing Inc., 1982 (4 pages).
File History for U.S. Appl. No. 11/153,252, Jun. 15, 2005 through Aug. 6, 2008 (220 pages).
File History for U.S. Appl. No. 11/193,032, Jul. 29, 2005 through Jul. 21, 2009 (254 pages).
File History for U.S. Appl. No. 11/241,237, Sep. 30, 2005 through Nov. 16, 2010 (136 pages).
File History for U.S. Appl. No. 12/175,281, Jul. 17, 2008 through Oct. 5, 2011 (122 pages).

(Continued)

Primary Examiner — Aaron J Kosar
(74) Attorney, Agent, or Firm — Pauly, DeVries Smith & Deffner LLC

(57) ABSTRACT

Embodiments herein relate to compositions herein can include one or more of a tomato extract, a rhubarb extract, a garlic extract, a cashew shell composition, and a saponin composition, wherein the composition prevents or reduces methanogenesis in animals. Embodiments herein also relate to compositions including one or more of glycoalkaloids, saponins, anthraquinones, anacardic acid, and allicin and methods for using the same for mitigating methanogenesis in animals. In an embodiment, a composition can include glycoalkaloids, such as α-tomatine, that can prevent methanogenesis. In an embodiment, a method of processing animal feed is included. In an embodiment, a method of treating an animal to reduce methanogenesis is included. Other embodiments are also included herein.

19 Claims, 3 Drawing Sheets

(56) References Cited

U.S. PATENT DOCUMENTS

| | | | |
|---|---|---|---|
| 5,219,596 | A | 6/1993 | Smith et al. |
| 5,496,571 | A | 3/1996 | Blagdon et al. |
| 6,475,527 | B1 | 11/2002 | Anderson et al. |
| 6,761,911 | B2 | 7/2004 | Anderson et al. |
| 7,416,742 | B2 | 8/2008 | McNeff et al. |
| 7,544,376 | B2 | 6/2009 | McNeff et al. |
| 7,641,920 | B2 | 1/2010 | Taylor, Jr. et al. |
| 8,043,633 | B2 | 10/2011 | McNeff et al. |
| 10,695,393 | B2 | 6/2020 | McNeff et al. |
| 2003/0039703 | A1 | 2/2003 | Anderson et al. |
| 2006/0003022 | A1 | 1/2006 | McNeff et al. |
| 2006/0024387 | A1 | 2/2006 | McNeff et al. |
| 2006/0073194 | A1 | 4/2006 | Taylor et al. |
| 2008/0274211 | A1 | 11/2008 | McNeff et al. |
| 2009/0285931 | A1 | 11/2009 | Shelby et al. |
| 2018/0333450 | A1 | 11/2018 | McNeff et al. |

OTHER PUBLICATIONS

File History for U.S. Appl. No. 15/978,397 downloaded Oct. 14, 2021 (137 pages).
"Milk Production and Biosynthesis," University of Guelph, http://web.archive.org/web/19981202101633/http://www.foodsci.uoguelph.ca/dairyedu/biosynthesis.html (Web Publication Date: Dec. 2, 1998), 5 pages.
Anderson, R. C., et al. "Effect of Sodium Chlorate on *Salmonella typhimurium* Concentrations in the Weaned Pig Gut," Journal of Food Protection, vol. 64, No. 2, pp. 255-258, 2001 (4 pages).
Asres, K., et al. "In vitro Antiprotozoal Activity of Extract and Compounds from the Stem Bark of Combretum molle," Phytotherapy Research 15, 613-617 (2001), 5 pages.
Barker, John, et al. "Survival of *Escherichia coli* 0157 in a soil protozoan: implications for disease," FEMS Microbiol. Lett. 173(2), 291-295, 1999 (5 pages).
Bonyata, Kelly "How Does Milk Production Work?," Kelly's Attachment Parenting, http://web.archive.org/web/20030620083858/http://www.kellymom.com/bf/supply/milkproduction.html (Web Publication Date: Jun. 20, 2003), 5 pages.
Boyaka, Prosper N, et al. "Oral QS-21 Requires Early IL-4 Help for Induction of Mucosal and Systemic Immunity," J Immunol Feb. 15, 2001, 166 (4) 2283-2290 (8 pages).
Brown, Sylvia, et al. "The Nursing Mother's Diet," Pregnancy.org, http:/web.archive.org/web/20040127064545/http://www.pregnancy.org/article.php?SID=1044 (Web Publication Date: Jan. 27, 2004), 3 pages.
Burkey, T. E., et al. "Effect of Dietary Mannanoligosaccharide and Sodium Chlorate on the Growth Performance, Acute-Phase Response, and Bacterial Shedding of Weaned Pigs Challenged with *Salmonella enterica* Serotype Typhimurium," J. Anim. Sci 82(2) 397-404 (Feb. 1, 2004), 8 pages.
Callaway, T. R, et al. "Sodium chlorate supplementation reduces *E. coli* 0157:H7 populations in cattle," J Anim Sci. Jun. 2002;80(6):1683-1689 (7 pages).
Cheeke, P. R "Actual and Potential Applications of Yucca schidigera and Quillaja saponaria Saponins in Human and Animal Nutrition," Proceedings of the American Society of Animal Science, 1999 (10 pages).
Choat, W. T., et al. "Effect of Conventional vs. Restricted Adaptation to a High-Concentrate Diet on Performance and Carcass Characteristics of Feedlot Calves," Animal Science Research Report, 2001 (4 pages).
Dehority, Burk A "Evaluation of Subsampling and Fixation Procedures Used for Counting Rumen Protozoa," Appl. Environ. Microbiol. 48(1), Jul. 1984, 182-185 (4 pages).
Dumitru, Razvan, et al. "Targeting Methanopterin Biosynthesis To Inhibit Methanogenesis," Appl. Environ. Microbiol. 69(12), Dec. 2003, 7236-7241 (6 pages).
Eschenlauer, S. C.P, et al. "Ammonia Production by Ruminal Microorganisms and Enumeration, Isolation, and Characterization of Bacteria Capable of Growth on Peptides and Amino Acids from the Sheep Rumen," Appl. Environ. Microbiol. 68(10), Oct. 2002, 4925-4931 (7 pages).
Fahmy, Wael G, et al. "Effect of Defaunation and Amino Acid Supplementation on Growth and Amino Acid Balance in Sheep," http://www.traill.uiuc.edu/dairynet/paperDisplay.cfm?ContentID=238, Aug. 5, 1998 (2 pages).
Francis, George, et al. "The biological action of saponins in animal systems: a review.," Br. J. Nutr. (2002), 88, 587-605 (19 pages).
Garcia-Lopez, P. M "In Vitro Inhibition of Microbial Methane Production by 9,10-Anthraquinone," J. Anim. Sci. 1996, 74:2276-2284 (9 pages).
Goel, G., et al. "Effects of Capric Acid on Rumen Methanogenesis and Biohydrogenation of Linoleic and a-Linolenic Acid," Animal (2009), 3:6, pp. 810-816 (7 pages).
Goodall, S. R., et al. "Sarsaponin Effects Upon Ruminal VFA Concentrations and Weight Gain of Feedlot Cattle," J. Anim. Sci. 49 (abstract only), 1979 (2 pages).
Goodall, S. R., et al. "Rumensin with and without Sarsaponin for Finishing Feedlot Steers," Col. Agr. Exp. Station 700 (1981), 4 pages.
Goodall, S. R., et al. "Sarsaponin in Beef Cattle Rations," Beef Nutrition Research (1978): 9-10 (2 pages).
Goodall, S. R., et al. "The Effect of Sarsaponin with and without Rumensin in High-Energy Rations," Col. Agr. Exp. Station 700 (1981), 6 pages.
Grant, R. J, et al."Feeding Dairy Cattle for Proper Body Condition Score," University of Missouri Agricultural Publication G3170, 1999 (5 pages).
Hoffman, D. J., et al. "The Effects of Zeranol and Munensin on Feedlot Steers," Proceedings, Western Section, American Society of Animal Science. vol. 28, 204-207 (1977), 4 pages.
Hoppe, Karl "Consequences of Underfeeding Beef Cows," http://www.ag.ndsu.edu/pubs/ansci/beef/coping/underfed.htm, 2009 (3 pages).
Hristov, A. N, et al. "Fermentation Characteristics and Ruminal Ciliate Protozoal Populations in Cattle Fed Medium- or High-Concentrate Barley-Based Diets," J. Anim. Sci. 2001. 79:515-524 (10 pages).
Hristov, Alexander N, et al. "Effect of Yucca schidigera on Ruminal Fermentation and Nutrient Digestion in Heifers," J. Anim Sci. 77(9), 2554-2563 (1999), 10 pages.
King, Christopher H, et al. "Survival of Coliforms and Bacterial Pathogens within Protozoa during Chlorination," Appl. Environ. Microbiol. 54(12), 3023-3033 (11 pages).
Klita, P. T, et al. "Effects of alfalfa root saponins on digestive function in sheep," J. Animal Sci. 74(5), 1144-1156 (13 pages).
Koenig, K. M, et al. "Effects of Protozoa on Bacterial Nitrogen Recycling in the Rumen," J. Anim Sci. 2000. 78:2431-2445 (15 pages).
Lila, Z. A, et al. "Effect of Sarsaponin on Ruminal Fermentation with Particular Reference to Methane Production in Vitro," J. Dairy Sci. 86:3330-3336 (2003), 7 pages.
Lu, C. D, et al. "Alfalfa Saponins Affect Site and Extent of Nutrient Digestion in Ruminants," J. Nutr. 17(5), 919-927 (1987), 9 pages.
Luginbuhl, J M, et al. "Forage Needs for Meat Goats and Sheep," http://web.archive.org/web/20010104120900/http://www.cals.ncsu.edu:80/an_sci/extension/animal/meatgoat/MGFrgnds.htm (Web Publication Date: Jan. 4, 2001), 6 pages.
Ly, T. M, et al. "Ingested Listeria monocytogenes Survive and Multiply in Protozoa," J. Med. Microbiol. 33(1) 1990, 51-54 (4 pages).
Maday, John "Assault on Pathogens," Drovers (www.drovers.com/news_editorial.asp?pgID=676&ed_id=2499), Feb. 12, 2004 (4 pages).
Mendoza, G. D, et al. "Influence of Ruminal Protozoa on Site and Extent of Starch Digestion and Ruminal Fermentation," J. Anim Sci. 1993. 71:1572-1578 (7 pages).
Miller, Terry L, et al. "Inhibition of Growth of Methane-Producing Bacteria of the Ruminant Forestomach by Hydroxymethylglutaryl-SCoA Reductase Inhibitors," J. Dairy Sci. 84(6) 1445-1448 (2001), 4 pages.
Murphy, K. D., et al. "Effects of Rearing Diet, Age at Freshening, and Lactation Feeding System on Performance," J. Dairy Sci. 74:2708-2717 (1991), 10 pages.

(56) References Cited

OTHER PUBLICATIONS

Navas-Camacho, Alberto, et al. "Effect of Reducing the Rumen Ciliate Protozoa Population by Feeding Saponin-Containing Plants on Rumen Function of Sheep Fed on Wheat Straw," Arch. Latinoam. Prod. Anim. 5(Supl. 1): 98-101 (1997), 4 pages.

Oldick, B. S, et al. "Compartmental Modeling with Nitrogen-15 to Determine Effects of Degree of Fat Saturation on Intraruminal N Recycling," J. Anim. Sci. 2000. 78:2421-2430 (10 pages).

Oldick, B. S, et al. "Effects of Degree of Fat Saturation on Fiber Digestion and Microbial Protein Syntehsis when Diets are Fed Twelve Times Daily," J. Anim. Sci. 2000. 78:2412-2420 (9 pages).

Rasmussen, M. A. "Microbial Factors/Pathogenesis of Subacute Rumen Acidosis (SARA) in Cattle to Assure Food Safety," Project No. 3625-31320-001-00D, National Animal Disease Center, ARS/USDA, 2005 (1 page).

Rasmussen, Mark A, et al. "Escherichia coli O157:H7 and the Rumen Environment," E. coli O157 in Farm Animals (CAB International 1999), 11 pages., 39-49.

Rush, Ivan, et al. "Grain Tempering Agent (SarTemp) for Corn in Finishing Rations," Beef Cattle Report (1993): 63-64 (3 pages).

Taylor, Stephanie J, et al. "Infection of Acanthamoeba castellanii with Mycobacterium bovis and M. bovis BCG and Survival of M. bovis within the Amoebae," Appl. Environ. Microbiol. 69(7), 4316-4319, 2003 (4 pages).

Towne, Gene, et al. "Omasal Ciliated Protozoa in Cattle, Bison, and Sheep," Appl. Environ. Microbiol. 56(2), 409-412 (1990), 4 pages.

Uematsu, Yoko, et al. "Spectrophotometric Determination of Saponin in Yucca Extract Used as Food Additive," Journal of AOAC International 83(6), 1451-1454 (2000), 4 pages.

Valdez, F. R, et al. "Effect of Steroidal Sapogenins on Ruminal Fermentation and on Production of Lactating Dairy Cows," J. Dairy Sci. 69(6), 1568-1575 (1986), 8 pages.

Wallace, R. J "Influence of Yucca Shidigera Extract on Ruminal Ammonia Concentrations and Ruminal Microorganisms," Appl. Environ. Microbiol. 60(6), 1762-1767 (1994), 6 pages.

Wang, Y., et al. "Effect of Steroidal Saponin from Yucca schidigera Extract on Ruminal Microbes," J. Appl. Microbiol. 88(5), 887-896 (2000), 10 pages.

Wang, Y., et al. "Effects of Yucca Schidigera extract on fermentation and degradation of steroidal sponins in the rumen simulation technique (RUSITEC)," Animal Feed Sci. Technol. 74(2), 143-153 (1998), 11 pages.

Wattiaux, Michel A., et al. "Chapter 1: Digestion in the Dairy Cow," The Babcock Institute for International Dairy Research and Development—The University of Wisconsin Madison. http://babcock.wisc.edu/downloads/de_html/ch01.en.html, 2007 (4 pages).

Wilson, R. C, et al. "Effects of Yucca shidigera Extract and Soluble Protein on Performance of Cows and Concentrations of Urea Nitrogen in Plasma and Milk," J. Dairy Sci. 81(4), 1022-1027 (1998), 6 pages.

Zinn, R. A, et al. "Influence of tempering on the feeding value of rolled corn in finishing diets for feedlot cattle," J. Anim Sci. 76(9), 2239-2246 (1998), 8 pages.

* cited by examiner

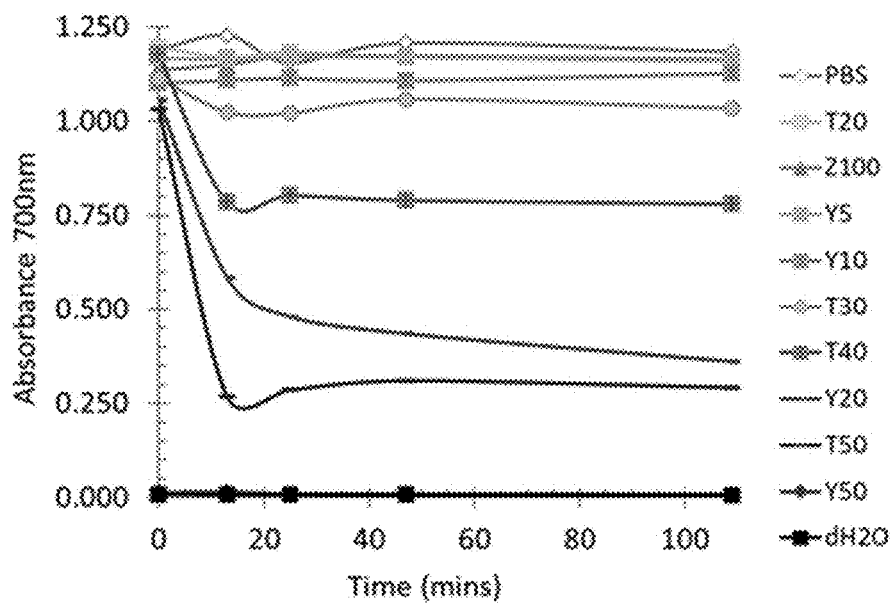

FIG. 1. Hemolysis activity monitored using a cell density assay measuring absorbance at 700nm. PBS-phosphate buffered saline (negative control), T20-Tomato leaf extract 20ug/mL, Z100-Zhi mu extract 100 ug/mL, Y5-yucca extract 5 ug/mL, Y10-yucca extract 10 ug/mL, T30-Tomato leaf extract 30 ug/mL, T40-Tomato leaf extract 40 ug/mL, Y20-Yucca extract 20 ug/mL, T50-Tomato leaf extract 50 ug/mL, Y50-Yucca extract 50 ug/mL, dH20-Deionized water (positive control).

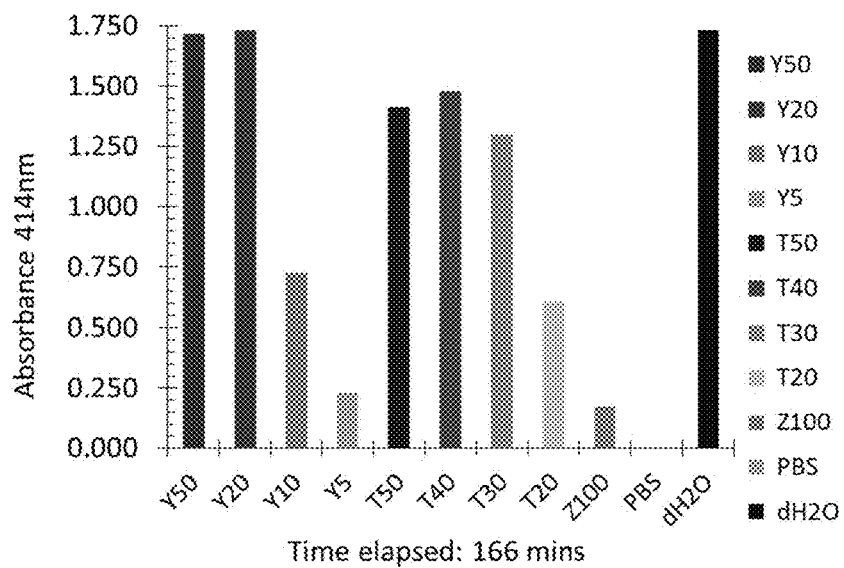

FIG. 2. Hemolytic activity monitored by measuring the release of hemoglobin from red blood cells. PBS-phosphate buffered saline (negative control), T20-Tomato leaf extract 20ug/mL, Z100-Zhi mu extract 100 ug/mL, Y5-yucca extract 5 ug/mL, Y10-yucca extract 10 ug/mL, T30-Tomato leaf extract 30 ug/mL, T40-Tomato leaf extract 40 ug/mL, Y20-Yucca extract 20 ug/mL, T50-Tomato leaf extract 50 ug/mL, Y50-Yucca extract 50 ug/mL, dH20-Deionized water (positive control).

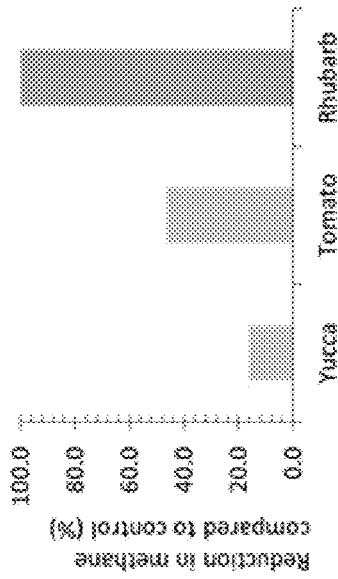

Figure 3. Effect of plant extracts on methane peak area utilizing in vitro batch fermentation and GC-MS analysis. Concentration of plant extracts used 2mg/mL (2000ppm). All treatments contained <2.0% DMSO as solvent.

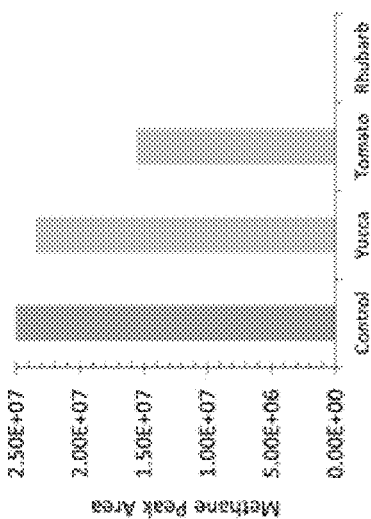

Figure 4. Percent reduction in methane production compared with control. Concentration of plant extracts used 2mg/mL (2000ppm). All treatments contained <2.0% DMSO as solvent.

COMPOSITIONS WITH AGENTS FOR MITIGATING METHANOGENESIS IN ANIMALS AND RELATED METHODS

This application claims the benefit of U.S. Provisional Application No. 63/082,906, filed Sep. 24, 2020, the content of which is herein incorporated by reference in its entirety.

FIELD

Embodiments herein relate to compositions including various naturally derived compounds and methods for using the same for mitigating methanogenesis in animals.

BACKGROUND

Ruminant livestock holds a significant place in modern food production. They possess the exceptional ability to digest plant cellulose and hemi-cellulose that humans are unable to digest and convert them into meat and milk. The increasing demand of ruminant food products in the form of meat and dairy to feed the expanding populations of the world has led to their occupying 30% of the Earth's land mass and consuming 30% of all agricultural crops produced.

Although ruminants have the ability to digest plant material typically unsuitable for human consumption, the majority of the rations animals are fed consist of high energy concentrates that are typically made from different grains, corn, and beans, products that can also be used by humans for food and in the production of several industrial biofuels such as ethanol and biodiesel. The purpose of these concentrates allows for increased weight gain as well as for the reduction in the amount of methane produced by the ruminant, yet carries several negative outcomes such as decreased fiber digestion, reduction in dry matter intake, and development of ruminal acidosis. There is therefore a current need for the development of naturally derived feed additives that reduce methane production, and increase feed efficiency.

Humanity's reliance on livestock for food is faced with the reality that fermentation of feedstuffs by ruminant animals contributes to the release of 75 teragrams of methane into the atmosphere each year. Ruminants account for 15% of total methane emissions and 51% of all anthropogenic sources. Although atmospheric methane concentrations are lower than carbon dioxide, methane is well known to have twenty-five times greater greenhouse effect. The accumulation of greenhouse gasses, like methane, contributes to global warming and is linked to climate change, threatening ecosystem viability, and agricultural productivity across the globe. Recent estimates indicate an annual increase in methane emissions by 30-40 million tons (27-36 teragrams) annually.

The widespread use of antibiotics has revolutionized livestock production. From the beginning of their use in the mid 1940's until the present day, antibiotics have helped treat numerous infections afflicting beef, poultry, and swine. They have also been used as growth promoters due to their ability to influence the microbiota inhabiting the rumen, resulting in improved weight gain and reduction in methane emissions. Today in the United States an estimated 14,788 tons of antimicrobials were sold to animal farmers for therapeutic and sub-therapeutic use.

However, over the last decade the use of antibiotics in animal production has come under increased scrutiny due to the link between their use and the emergence of antibiotic resistant bacteria. Accordingly, the CDC released a statement in 2013 stating "because of the link between antimicrobial use in food-producing animals and the occurrence of antimicrobial-resistant infections in humans, antimicrobials should be used in food-producing animals only under veterinary oversight and only to manage and treat infectious diseases, not to promote growth." On Jan. 1, 2017 the FDA put forth legal directives requiring all antibiotics used for animal agriculture to change from over the counter to Rx or veterinary feed directive (VFD), preventing the use of antibiotics critical to human medicine from being used in animal production without veterinary prescription, limited their use for health emergencies and ending their use as growth promoters. Given the increased regulation of antibiotic use in livestock production, there is a need for the discovery of new natural products capable of economically modulating the microbiota of ruminant animals.

SUMMARY

Embodiments herein relate to compositions including one or more of a tomato extract, a rhubarb extract, a garlic extract, a cashew shell composition, and a saponin composition, wherein the composition prevents or reduces methanogenesis in animals.

Embodiments herein also relate to compositions including one or more of glycoalkaloids, saponins, anthraquinones, anacardic acid, and allicin and methods for using the same for mitigating methanogenesis in animals.

In an embodiment, a method of processing animal feed is included. The method can include contacting an animal feed material with a composition described herein.

In an embodiment, a method of treating an animal to reduce methanogenesis is included. The method can include administering an effective dose of a composition described herein to the animal.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which:

FIG. 1 is a graph showing absorbance versus time for a cell density assay conducted on various compositions.

FIG. 2 is a graph showing absorbance versus time for a hemoglobin assay conducted on various compositions.

FIG. 3 is a graph showing the effects of plant extracts on methane peak area utilizing in vitro batch fermentation and GC-MS analysis.

FIG. 4 is a graph showing the percent reduction in methane production for plant extracts compared with a control.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

As described above, fermentation of feedstuffs by ruminant animals contributes to the release of 75 teragrams of methane into the atmosphere each year. Ruminants account for 15% of total methane emissions and 51% of all anthropogenic sources. Although atmospheric methane concentrations are lower than carbon dioxide, methane is well known to have twenty-five times greater greenhouse effect.

However, compositions herein can be used to reduce and/or inhibit methanogenesis in animals. In particular, compositions herein including glycoalkaloids are useful for mitigating methanogenesis in animals.

While not intending to be bound by theory, it is known that methanogenic bacteria living in the rumen of some animals produce methane gas through a process called methanogenesis. In addition, ruminal protozoa have been shown to produce hydrogen in the rumen, which is utilized by the methanogens to produce methane. Compositions herein are believed to impact both methanogenic bacteria and ruminal protozoa.

In an embodiment, compositions herein can include one or more of a tomato extract; a rhubarb extract; a garlic extract; and a saponin composition. In some embodiments, the composition can include two or more, or three or more of those components. In some embodiments, compositions used with the embodiments herein, can include glycoalkaloids and, in some cases, other components as described herein. For example, compositions herein can also include one or more of saponin compositions, garlic-derived components, rhubarb-derived components, cashew shell derived components, and the like. In some embodiments, compositions included herein can be mixed in with animal feed material. In this manner, the composition can act as a feed conditioning agent. Therefore, in an embodiment, the invention includes a feed conditioning composition including one or more glycoalkaloids.

Compositions included with embodiments herein can be formulated in various ways. For example, compositions herein can be formulated as a liquid, slurry, dry powder, dry granular mix, paste, pellets, block, or the like. Compositions herein can be administered to an animal as a pill, a bolus, a liquid drench, or the like.

In accordance with embodiments included herein, compositions including glycoalkaloids can be administered to an animal along with the animal's feed ration. For example, a composition, such as a liquid or solid composition can be mixed in with an animal's feed ration. In some embodiments, a composition, such as a liquid composition, can be mixed in with an animal's water.

Glycoalkaloids are a family of chemical compounds derived from alkaloids to which sugar groups are appended. The alkaloidal portion of the glycoalkaloid is also generically referred to as an aglycone. Glycoalkaloids are typically bitter tasting. In some embodiments herein, the glycoalkaloids utilized can specifically include nitrogen-containing glycoalkaloids.

Tomato leaves contain the glycoalkaloid α-tomatine at concentrations as high as 975 mg/kg fresh weight. α-tomatine is structurally comprised of a spirostan steroidal alkaloid aglycone, tomatidine, attached at the 3rd carbon to the sugar tetramer lycotetraose.

The amount of glycoalkaloids or specific examples thereof such as α-tomatine administered can vary based on factors such as the size of the animal, the type of feed being fed to the animal, and the like. In various embodiments, the dosage of glycoalkaloids and/or specific glycoalkaloids (such as α-tomatine) can be greater than or equal to 100 mg, 500 mg, 2.5 g, 4.5 g, 6.5 g, 8.5 g, 10 g, 15 g, 20 g, 50 g, 100 g, 250 g, 500 g, or more, or can be an amount falling within a range between any of the foregoing. The amount of glycoalkaloids and/or specific examples thereof in the overall composition herein can be at least 0.1, 0.5, 1, 2.5, 5, 10, 15 or 20 wt. percent.

In some embodiments, compositions herein can include a garlic component, such as a garlic extract, garlic leaves or garlic leaf extract, garlic oil. In some embodiments, compositions herein can include a garlic compound such as one or more of allicin, diallyl disulfide, allyl mercaptan, and diallyl sulfide.

In various embodiments, the dosage of the garlic component and/or specific examples thereof (such as allicin, diallyl disulfide, allyl mercaptan, and diallyl sulfide) can be greater than or equal to 100 mg, 500 mg, 2.5 g, 4.5 g, 6.5 g, 8.5 g, 10 g, 15 g, 20 g, 50 g, or more, or can be an amount falling within a range between any of the foregoing. The amount of garlic components and/or specific examples thereof in the overall composition herein can be at least 0.1, 0.5, 1, 2.5, 5, 10, 15 or 20 wt. percent.

In some embodiments, compositions herein can include a rhubarb component, such as a rhubarb extract, rhubarb root, rhubarb leaf, or the like. In some embodiments, compositions herein can include a rhubarb compound such as one or more anthraquinones found in rhubarb. The three main anthraquinones in rhubarb are emodin, aloe-emodin, and rhein. In some embodiments, compositions herein can specifically include 2-chloroanthraquinone.

In various embodiments, the dosage of the rhubarb component and/or specific examples thereof (such as the three main anthraquinones in rhubarb and/or 2-chloroanthraquinone) can be greater than or equal to 100 mg, 500 mg, 2.5 g, 4.5 g, 6.5 g, 8.5 g, 10 g, 15 g, 20 g, 50 g, or more, or can be an amount falling within a range between any of the foregoing. The amount of rhubarb components and/or specific examples thereof in the overall composition herein can be at least 0.1, 0.5, 1, 2.5, 5, 10, 15 or 20 wt. percent.

In some embodiments, compositions herein can include a cashew component, such as a cashew nut shell extract (CNSE) or cashew nut shell oil, or the like. CNSE is a byproduct of cashew farming, and contains anacardic acid, a salicylic acid derivative with a C15 tail that has the ability to disrupt bacterial membranes.

In various embodiments, the dosage of the cashew component and/or specific examples thereof (such as anacardic acid) can be greater than or equal to 100 mg, 500 mg, 2.5 g, 4.5 g, 6.5 g, 8.5 g, 10 g, 15 g, 20 g, 50 g, or more, or can be an amount falling within a range between any of the foregoing. The amount of cashew components and/or specific examples thereof in the overall composition herein can be at least 0.1, 0.5, 1, 2.5, 5, 10, 15 or 20 wt. percent.

Various compositions herein can also include one or more saponins and/or saponin compositions. Saponins are natural plant surfactants that occur in over 500 different plant species belonging to some 80 different families. They are generally recognized by their strong foaming action when placed in water, which has made them especially useful in the manufacture of foods, beverages, shampoos, wetting agents and pharmaceuticals.

Saponins are classified as surfactants because they have both lipophilic and hydrophilic "regions." Thus, the surfactant activity of saponins is a result of both fat-soluble and water-soluble moieties in the same molecule. The lipophilic region may be a steroid, triterpene, or alkaloid, and is termed a sapogenin. The hydrophilic "region" contains one or more water-soluble carbohydrate side chains. The structural complexity of saponins is derived largely from the carbohydrate portion of the molecule due to the many different types of possible side chain carbohydrates, such as glucose, xylose, galactose, pentose or methylpentose, which may have different connectivity and/or anomeric configuration.

Saponins can play a role in reducing or eliminating ruminal protozoa. Saponins (triterpenoid, steroidal, or alkaloid) have a hemolytic action that is believed to be related to their affinity for cell membrane sterols that are embedded in the lipid bi-layer, and in particular cholesterol. Saponins have been shown to form insoluble complexes with cholesterol and thereby open holes in cell membranes of ruminal protozoa to cause cell lysis. The ability of saponins to rupture cell membranes, but yet be non-toxic to mammals when ingested orally makes them a suitable protozoan eliminator for use in livestock.

Saponins useful in the present invention can be extracted from plants of the family: Agavaceae, genus: *Yucca*, such as *Yucca schidigera*. *Yucca* derived saponins generally have steroidal sapogenins. Sarsasapogenin is the major sapogenin found in the *Yucca schidigera* plant and thus *Yucca* extracts are rich in sarsaponins. Saponins useful in the present invention can also be extracted from plants of the family: Agavaceae, genus: *Agave*, which grows extensively in the southwestern United States and Mexico. Additional sources of saponins can include extracts of soybeans, fenugreek, peas, tea, yams, sugar beets, alfalfa, asparagus, aloe, vanilla, zhimu, *Sapindus saponaria*, citrus fruits (limonoid saponins) as well as from *Quillaja saponaria* bark.

The typical saponin content that naturally occurs in *Yucca* plants is from 0.1-2% saponins by weight. *Yucca* extracts can be derived by extracting *Yucca* powder with an aqueous solution that may or may not contain some fraction of organic solvent such as methanol, ethanol, propanol, butanol, or the like.

Commercially available *Yucca* extracts can have total solids content usually in the range from 5-50% solids by weight. The saponin content of a typical 50 brix (50% solids by weight) *Yucca* extract is usually in the range of about 1-2% saponins by weight as measured by HPLC analysis. Another method of measuring total saponin content is the extraction of all soluble components into a butanol extract followed by gravimetric analysis of the compounds dissolved in the butanol fraction. Measuring saponin content by the butanol extract method typically results in higher numbers than the more advanced HPLC method. Accordingly, the typical 50 brix (50% solids by weight) *Yucca* extract is usually in the range of about 5-20% saponins content by weight as measured by the butanol extract method.

In an embodiment, the composition herein can include at least 0.1% by weight saponins as measured by HPLC. In an embodiment, the composition can include at least 0.5% by weight saponins as measured by HPLC. In an embodiment, the composition can include at least 1.0% by weight saponins as measured by HPLC. In an embodiment, the composition can include at least 2.0% by weight saponins as measured by HPLC. In an embodiment, the composition can include at least 5.0% by weight saponins as measured by HPLC. In an embodiment, the composition can include at least 7.5% by weight saponins as measured by HPLC. In an embodiment, the composition can include at least 10.0% by weight saponins as measured by HPLC.

Animal Feed Materials

In an embodiment, the invention includes a method of processing animal feed including contacting an animal feed material with a composition including glycoalkaloids. By adding the composition to the animal feed, dosing can be simplified as the composition will reach the rumen along with the feed. In various embodiments, the animal feed material (including any of the materials described below) in combination with the composition is included. In various embodiments, a total mixed ration of animal feed material (including any of the materials described below) in combination with the composition is included.

It will be appreciated that animal feed materials can include many different components such as, but not limited to, alfalfa hay, alfalfa haylage, almond hulls, apple components, rolled barley, barley malt sprouts, barley silage, bermuda grass, blood meal, bluegrass, brome, canary grass, canola seed, canola meal, chocolate byproduct, dried citrus pulp, clover, sudangrass hay, dry-rolled corn, tempered-rolled corn, steam-flaked corn, ground shelled corn, cracked corn, hominy feed, corn gluten feed, corn silage, wet brewer's grain, dry brewer's grain, distillers grains (dried and wet), stillage, soybean meal, soybean seeds, soybean hulls, sunflower meal, sunflower oil, sunflower seeds, tomato products, wheat bran, rolled wheat, wheat hay, wheat middlings, wheat silage, whey, fescue, fish byproducts, hay, legumes, linseed, meat meal, meat and bone meal, rolled oats, oat hay, oat silage, orchard grass, peanut meal, potato byproduct meal, rice bran, rye, safflower, dry rolled sorghum, steam-flaked sorghum, sorghum silage, soybean hulls, whole cottonseed, cottonseed hulls, cottonseed meal, sugar beet pulp, dehydrated beet pulp, bakery waste, cottonseed meal, yellow grease, white grease, vegetable oil, palm oil, coconut oil, cottonseed oil, sunflower oil, flax seed oil, safflower oil, corn oil, soybean oil, sesame oil, canola oil, olive oil, tallow, water, hydrolyzed feather meal, cane molasses, sugar beet molasses, and the like, and combinations thereof. In various embodiments, combinations of the animal feed materials can be formulated as a total mixed ration.

In some embodiments, the animal feed material can specifically include byproducts of ethanol production. For example, in some embodiments, the animal feed material can specifically include distillers dried grains, distillers wet grains, and/or stillage.

It will be appreciated that methods and compositions of the invention can be used for the treatment of animals, including bovine, fowl, porcine, ovine, and equine species. By way of example, the methods and compositions of the invention can be used for the treatment of cattle, chickens, turkeys, ducks, quail, geese, pigs, and sheep. In a specific embodiment, the methods and compositions of the invention can be used for the treatment of ruminants.

In an embodiment, a method of treating an animal to reduce methanogenesis is included. The method can include administering an effective dose of a composition to the animal. The composition can include glycoalkaloids and, in particular, α-tomatine.

In some embodiments the method can further include selecting an animal exhibiting signs of elevated methanogenesis. In some embodiments the animal can be a ruminant. In some embodiments the animal can be *Bos taurus*.

It will be appreciated that compositions in accordance with embodiments herein can include various additives. By way of example, compositions can also include additives such as water, propylene glycol, Vitamin E (as di-alpha-tocopheryl acetate), Vitamin A Propionate, Vitamin A Palmitate, Vitamin B1, Vitamin B2, Vitamin B6, Vitamin B12, D-Activated Animal Sterol (source of Vitamin D3), yeast components, dried egg solids, dried casein, and dried whey, amongst others.

EXAMPLES

Example 1: Lysing Red Blood Cells

Extracts of tomato leaves, zhi mu root, and *Yucca* whole plant were tested for their ability to lyse red blood cells based on a cell density assay (see FIG. 1). The tomato and *yucca* extracts were shown to effectively lyse a 0.2% red blood cell solution, whereas the zhi mu extract did not show any activity. In this experiment, a 50% hemolytic dose ("HD50") was obtained at tomato leaf concentrations of 40-50 ug/mL and 10-20 ug/mL for the *Yucca* extract. This example shows that tomato leaf materials can effectively lyse cells.

Example 2: Hemoglobin Assay

The extracts were further subjected to a hemoglobin assay (see FIG. 2). This assay detects the amount of hemoglobin released into the solution following cell lysis. The results here indicate the high hemolytic activity of *yucca* extract and tomato leaf extract, with a low level of activity recorded for the zhi mu extract. The results are consistent with what was observed in the cell density assay validating the lysis of cellular membrane detected by the decreased cellular densities in FIG. 1.

The HD50 for *Yucca* was 10-20 ug/mL and the HD50 for tomato leaf was 20-30 ug/mL. The decrease in HD50 for the tomato extract for the hemoglobin release experiment versus the cell density is interesting as it indicates the ability for hemoglobin to diffuse from within the red blood cells without requiring cell lysis. This may indicate partial degradation of cell membranes by the tomato extract or of membrane permeabilization allowing for hemoglobin escape. The ability to initiate passive diffusion is similar to the mechanism of action of monensin, a commonly used ionophore for defaunation of cattle rumen, whereby the membrane permeabilizing and ion chelating effects allow for the transfer of ions within the protozoal cytoplasm and the disruption of ion gradients leading to cellular death. One main advantage over using monensin is the ability to also release cytoplasmic proteins and primary metabolites which would increase effectiveness of antiprotozoal activity.

Example 3: Effects of Compositions on Methane Production

The effects of different compositions on methane production was assessed using the following procedure:
1. The rumen fluid was collected from the bottom of the rumen and squeezed through cheesecloth to remove large food particles. The rumen liquor was collected by funnel and transferred into a pre warmed insulated collection vessel. The vessel is filled near the top to prevent oxygen from entering the headspace.
2. A plastic tray was filled with ½" water and placed in the incubator with the temperature set to 40 C.
3. Four hundred milligrams of cattle feed was massed and transferred to each fermentation vessel. (The cattle feed was previously dehydrated at 90 C and ground through 1.4 mm screen).
4. Warm water was added to a large cooler and the fermentation vessels were placed there to maintain 40 C.
5. A large hot plate was set to maintain 40 C. On this hot plate was placed the rumen buffer liquid.
6. The rumen fluid mixing flask was placed on the hot plate and gas exchanged for carbon dioxide. Rumen fluid vessel was inverted several times to re-suspend microbes that may have sedimented to the bottom.
7. The rumen fluid (320 mL) was passed through four layers of cheesecloth in a funnel and into the rumen fluid mixing flask to further remove large food particulates. This may require scraping with a spoon to ensure proper fluid passage. A steady stream of carbon dioxide was applied from above.
8. The rumen buffer (640 mL) was then poured into the rumen fluid mixing flask at a ratio of 1:2 (rumen fluid:rumen buffer) and kept under constant stream of carbon dioxide.
9. The diluted rumen fluid was mixed and poured into a pre-warmed graduated cylinder. Sixty milliliters was measured and then transferred to a 120 mL fermentation vessel, at this point the treatment is added (see sections 12-16), the sample headspace was exchanged with anaerobic carbon dioxide, and the fermentation vessels are labeled according to the treatment they receive.
10. After the sample was gassed, it was sealed with an aluminum crimp top cap with butyl rubber stopper and placed into the incubator, making a note of the sample ID and the time placed in the incubator.
11. This process was repeated for each of the samples.

Treatment groups were as follows:
Control—DMSO only
*Yucca* Powder 2 mg/mL
Tomato extract 2 mg/mL
Rhubarb extract 2 mg/mL
   *All samples will have 2.0% DMSO=1.2 mL
   *All samples done in quadruplicate
   *Total number of samples 16

The treatment samples were prepared as follows:
1. To Prepare *Yucca* powder samples: To make a 100 mg/mL stock solution, a total of 4.8 mL was needed to have enough for each fermentation (1.2 mL×4). 6 mL was prepared by combining 600 mg extract powder with 6 mL DMSO. To each of the *Yucca* samples 1.2 mL of 100 mg/mL stock was added to give a final concentration of 2 mg/mL.
2. To Prepare Rhubarb samples: This extract in DMSO was concentrated to 100 mg/mL. To each of the rhubarb samples 1.2 mL of 100 mg/mL stock was be added to give a final concentration of 2 mg/mL.
3. To Prepare Tomato extract samples: This extract in DMSO was concentrated to 100 mg/mL. To each of the tomato samples 1.2 mL of 100 mg/mL stock was added to give a final concentration of 2 mg/mL.
4. To Prepare Control: To each of the control samples 1.2 mL of DMSO was be added to give a final DMSO concentration of 2.0%.

After 24 hrs the incubator heat source was switched off. A piece of tubing with two gas tight small diameter needles was used to transfer the pressurized gas in the fermentation vessels to a 20 mL glass collection vial fitted with butyl rubber septum and aluminum crimp top cap. The first needle was placed in the 20 mL collection vial, then the second needle in the fermentation vessel. The gas exchange was allowed to equilibrate for two minutes. This process is repeated for each sample.

The samples were then processed using GC-MS, in the order they were made. The GC-MS data was collected using a HP6890 equipped with HP 7694 Head-Space Sampler and with a 30 feet long ALLTECH HAYSEP D 100/120 0.125 in (o.d.), with 0.085 in (i.d.) packed column. The HS-GC-MS chromatographic conditions were: 1 mL injection volume; Head pressure: 5 psi, He flow rate 100 mL/min; Initial temp 50° C., hold for 15 min, ramp 20° C./min to 220° C. and hold for 10 min.

The results analyzing treatment of rumen fluid 24-hour batch fermentations with *yucca*, tomato leaf and rhubarb leaf extracts are shown in FIG. 3. It was found that methane production compared with control was reduced by 15.8%, 46.1%, and 100% for *Yucca* extract, tomato leaf extract, and rhubarb leaf extract respectively (FIG. 4). Rhubarb extract demonstrated remarkable ability to decrease methane emissions with a negligible decrease in carbon dioxide emissions of −0.2% (data not shown). Surprisingly the tomato leaf extract also lead to significant reductions in methane of 46.1%. This example shows that extracts such as *yucca*, tomato leaf, and rhubarb are effective inhibitors of methanogenesis.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications may be made while remaining within the spirit and scope herein. As such, the embodiments described herein are not intended to be exhaustive or to limit the invention to the precise forms disclosed in the following detailed description. Rather, the embodiments are chosen and described so that others skilled in the art can appreciate and understand the principles and practices.

The invention claimed is:

1. An animal feed composition comprising:
  one or more of
    a tomato extract;
    a rhubarb extract;
    a garlic extract;
    a cashew shell composition; and
    a saponin composition;
  wherein the composition prevents or reduces methanogenesis in animals.

2. The composition of claim 1, comprising at least two of
  a tomato extract;
  a rhubarb extract;
  a garlic extract;
  a cashew shell composition; and
  a saponin composition.

3. The composition of claim 1, comprising at least three of
  a tomato extract;
  a rhubarb extract;
  a garlic extract;
  a cashew shell composition; and
  a saponin composition.

4. The composition of claim 1, the tomato extract comprising a tomato leaf extract.

5. The composition of claim 1, the tomato extract comprising tomato-derived glycoalkaloids.

6. The composition of claim 1, the tomato extract comprising tomato-derived nitrogen containing glycoalkaloids.

7. The composition of claim 1, the tomato extract comprising α-tomatine.

8. The composition of claim 1, the composition comprising from 1 to 40 wt. percent of a tomato extract.

9. The composition of claim 1, the rhubarb extract comprising at least one of a rhubarb leaf extract or a rhubarb root extract.

10. The composition of claim 1, the rhubarb extract comprising rhubarb-derived anthraquinones.

11. The composition of claim 1, the rhubarb extract comprising one or more of emodin, aloe-emodin, and rhein.

12. The composition of claim 1, the composition comprising from 1 to 40 wt. percent of a rhubarb extract.

13. The composition of claim 1, the garlic extract comprising at least one of a garlic leaf extract and garlic oil.

14. The composition of claim 1, the garlic extract comprising allicin, diallyl disulfide, allyl mercaptan, and diallyl sulfide.

15. The composition of claim 1, the composition comprising from 1 to 40 wt. percent of a garlic extract.

16. The composition of claim 1, the saponin composition comprising a *yucca* extract.

17. The composition of claim 1, the saponin composition comprising sarsasponins.

18. The composition of claim 1, the composition comprising from 1 to 40 wt. percent of a saponin composition.

19. An animal feed product comprising:
  an animal feed material; and
  a composition, the composition comprising
    one or more of
      a tomato extract;
      a rhubarb extract;
      a garlic extract;
      a cashew shell composition; and
      a saponin composition.

* * * * *